United States Patent [19]

Weissman

[11] Patent Number: 5,040,977
[45] Date of Patent: Aug. 20, 1991

[54] SELF POWERED DENTAL PLAQUE-REMOVING DEVICE

[76] Inventor: Bernard Weissman, 225 E. 48th St., New York, N.Y. 10017

[21] Appl. No.: 353,999

[22] Filed: May 19, 1989

Related U.S. Application Data

[63] Continuation-in-part of Ser. No. 179,332, Apr. 8, 1988, Pat. No. 4,954,082.

[51] Int. Cl.⁵ .............................................. A61C 1/07
[52] U.S. Cl. .................................. 433/122; 433/125; 433/131; 433/133
[58] Field of Search ............... 433/122, 123, 124, 125, 433/131, 133

[56] References Cited

U.S. PATENT DOCUMENTS

| | | | |
|---|---|---|---|
| 656,124 | 8/1900 | Kinnison | 433/124 |
| 3,552,022 | 1/1971 | Axelsson | 433/122 |
| 3,939,599 | 2/1976 | Henry et al. | 433/131 |
| 4,276,025 | 6/1981 | Straihammer | 433/133 |
| 4,315,741 | 2/1982 | Reichl | 433/125 |
| 4,781,589 | 11/1988 | Bareth | 433/122 |

Primary Examiner—John J. Wilson
Attorney, Agent, or Firm—Paul J. Sutton; Barry G. Magidoff; Anthony Amaral

[57] ABSTRACT

This invention provides a self-powered dental hygiene device having an outer housing with three sections, a battery section at one end, an intermediate electric motor section and at the second end a transmission section with a head end section at the distal end. The head end section includes an aperture therethrough, transverse to the transmission section and designed to hold a replaceable dental tool, designed for reciprocating longitudinal motion. The casing is shaped such that the first battery section extends at an angle of between 7 and 12 degrees relative to the transmission section, and the aperture is preferably perpendicular to the axis of the transmission section. The dental tool bit held within the aperture has a hollow plenum for containing a fluid to be administered during use and a pressurizing means is secured to the tool to provide for the expression of the fluid through openings in the tool blade. There is also provided means to resiliently restrain the dental tool bit from rotating relative to the tool.

16 Claims, 7 Drawing Sheets

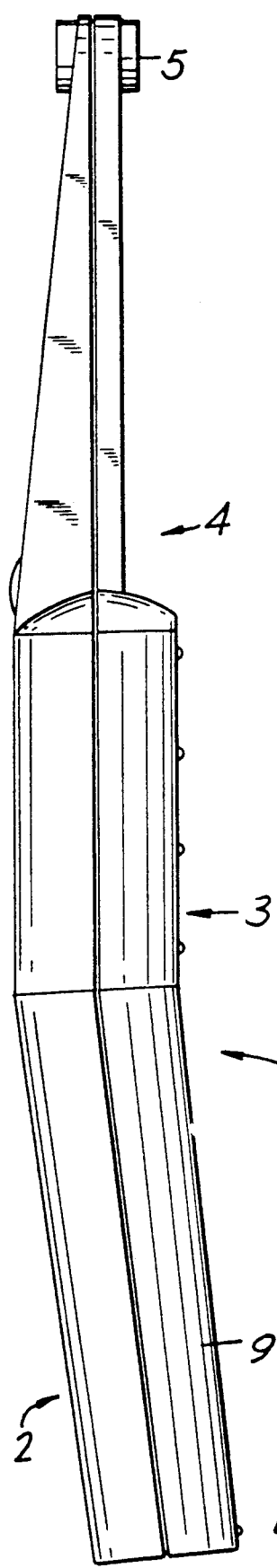
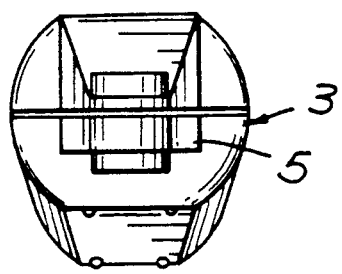
FIG. 5a
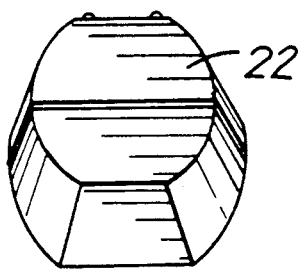
FIG. 5b
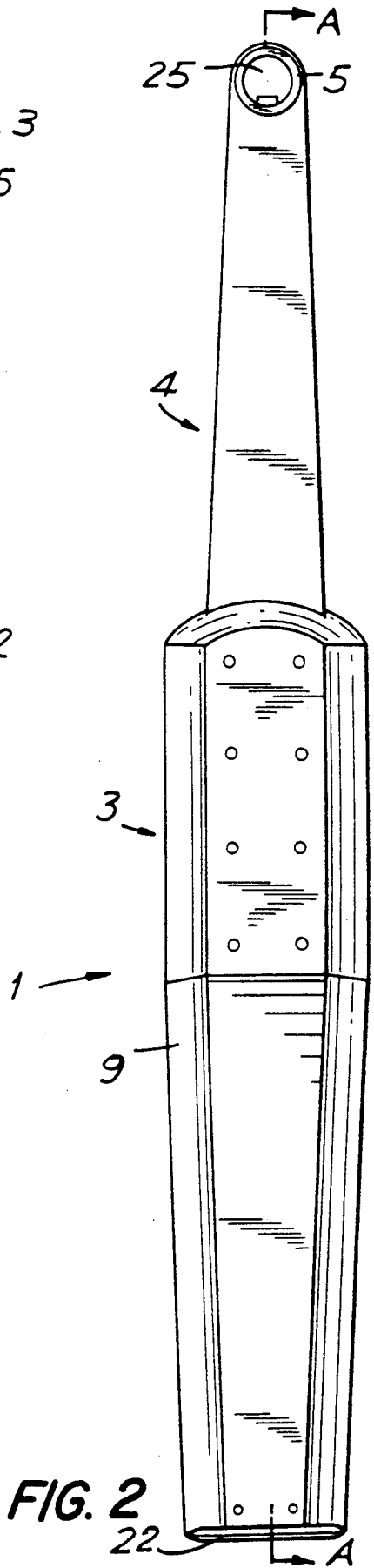

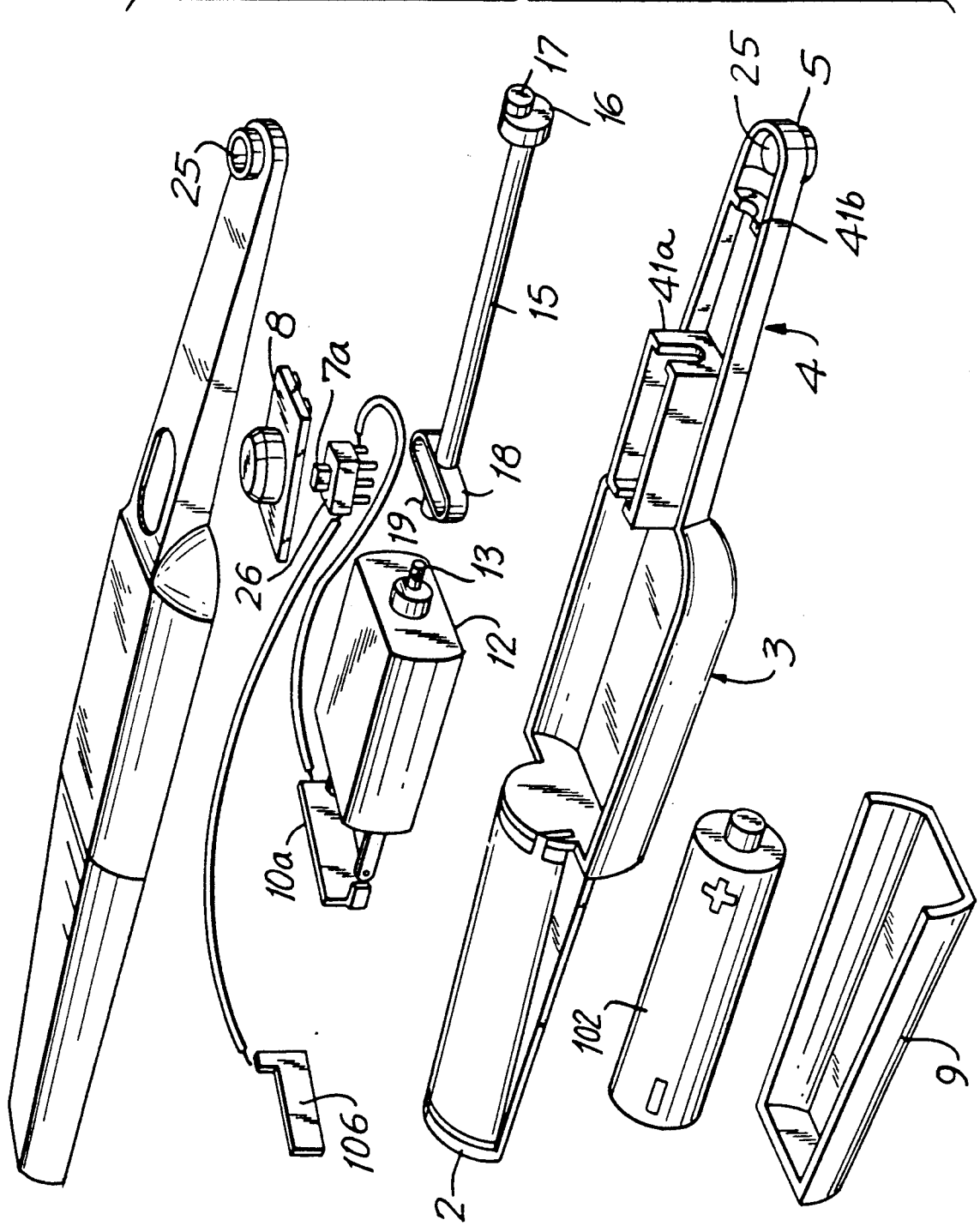

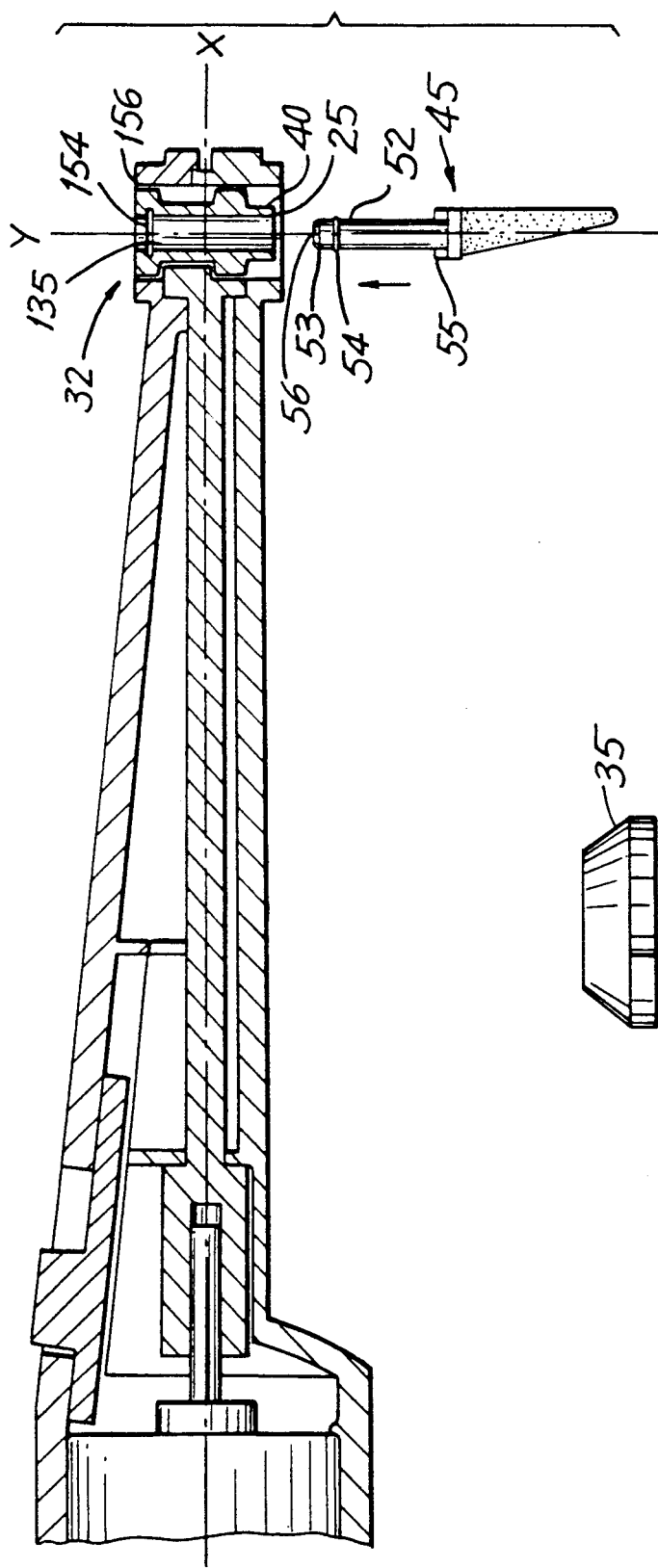

SELF POWERED DENTAL PLAQUE-REMOVING DEVICE

BACKGROUND OF THE INVENTION

This is a continuation-in-part of application Ser. No. 179,332, filed on Apr. 8, 1988, now U.S. Pat. No. 4,954,082.

The present invention relates to a hand-held, internally or self-powered, reciprocating plaque-preventing tool which permits safe use by the general consumer for personal dental hygiene. A removable plaque preventing tool bit is provided, preferably with means to pre-set the angular relationship between the tool bit and the handle, and can further be provided with internal means for simultaneously applying a fluid medium, such as dental cleaning paste, to teeth while reciprocating the bit, for cleaning or polishing the teeth.

There has previously been successfully provided a mechanically driven hand piece, which can be readily powered by a conventional rotary dental drill, to provide reciprocating motion of the type preferably used when abrading or filing teeth or removing excess restorative material, such as hardened dental amalgams or dental composite materials Such abrasive methods, depending upon the hardness of the abrasive material and the rapidity and pressure with which the abrading surface is applied, can be used to either remove hardened amalgam or dental enamel or to merely remove plaque and to clean and polish teeth surfaces, including both the major lingual and facial surfaces of teeth as well as the interproximal surfaces bordering the teeth interspaces.

A reciprocating handpiece which has been used, by dentists, powered by the dentist's office drill, e.g., is the device described in U.S. Pat. No. 3,552,022 to Axelsson, and commercially available as a Dentatus EVA Reciprocating Motor-Driven Handpiece; this has been used for both purposes, together with replaceable dental abrasive tool bits formed of, e.g., hardened or diamond-coated metal blades, or plastic blades with or without embedded abrasives.

It is also known to utilize a syringe type of device to apply toothpaste and the like material for dental hygienic cleaning prior to application of either a mechanically driven or manually operated tooth cleaning means, whether for clinical use or for home use. Such a device is shown, for example, in U.S. Pat. No. 4,411,623 to Axelsson.

SUMMARY OF THE INVENTION

It is an object of the present invention to provide a safe means for individuals to remove, by a reciprocating wiping tool, bacterial colonies and the nutrients film which can result in dental plaque formation, if not dislodged. It is a further object to provide means to assist such mechanical removal by providing means for simultaneously applying a cleaning fluid, or other therapeutic prophylactic medium, to the teeth while mechanically dislodging debris or polishing the teeth using a portable, self-powered, or battery operated, tool and to provide safe mechanical stimulation to the gums. It is a further object of the present invention to continuously administer such fluid medium through a disposable mechanically driven tool bit which can be hygienically filled and refilled during a single continuing procedure. It is a further object to provide a tool bit (for use with a powered handle) of a size, shape and material which can be molded of plastic sufficiently economically for one-time use, thus further reducing any risk of contagious infection.

It is also an object of the present invention to restrain relative rotation of the cleaning and stimulating tool bit under normal cleaning force, so as to permit accurate positioning and manipulation of the tool, while preventing injury from the accidental application of excessive force.

The self-powered dental hygiene device of the present invention comprises an outer housing having three sections: a first end section designed to hold an electric battery, a first intermediate section containing a rotary electric motor, a second intermediate section containing mechanical transmission means, and a second end head section, adjacent the transmission means and distal the electric motor, comprising means for holding a replaceable film-removing wiping tool bit. Electrical conducting means are provided between the battery section and the electric motor. The transmission means converts the rotary motion of the electric motor to reciprocating motion. Switch means are provided movably secured to the housing for completing and breaking an electric circuit between the battery section and the electric motor.

The replaceable tool bits can be hollow and secured to fluid pressure means on the housing for causing the flow of e.g., a cleaning fluid into and through the tool bit.

Limited restraining means for the tool bit can be provided in another preferred embodiment of this invention for presetting the angular relationship between the housing and the tool bit blade and for restraining rotation of the tool bit during operation, while providing for rotation of the bit upon the application of a greater than maximum permitted force; at such greater force, the restraint breaks away and the tool blade is permitted to rotate to avoid injury to the user. Such angular restraint is provided by interaction between the tool bit and holding means secured to the housing.

BRIEF DESCRIPTION OF THE DRAWINGS

Preferred embodiments of this invention are further described below, by way of example and not exclusion, by reference to the accompanying drawings which display certain portions of the present invention in schematic form. The details of such schematically shown portions will be readily known to those skilled in the art based upon the following verbal descriptions. Referring to the drawings:

FIG. 2 is a bottom view of the tool of FIG. 1;

FIG. 3 is a side view of the tool of FIG. 1;

FIG. 5a is a head view of the tool of FIG. 1;

FIG. 5b is a base view of the tool of FIG. 1;

FIG. 7 is an exploded isometric view of the tool of FIG. 1;

FIG. 11 is a cross-sectional partial side elevational view of the transmission and head portion of a second embodiment of the tool with a tool bit and a fixed collar; and FIG. 11a is an enlarged elevation view of the fixed collar of FIG. 11.

DETAILED DESCRIPTION OF PREFERRED EMBODIMENTS

Figure 1:
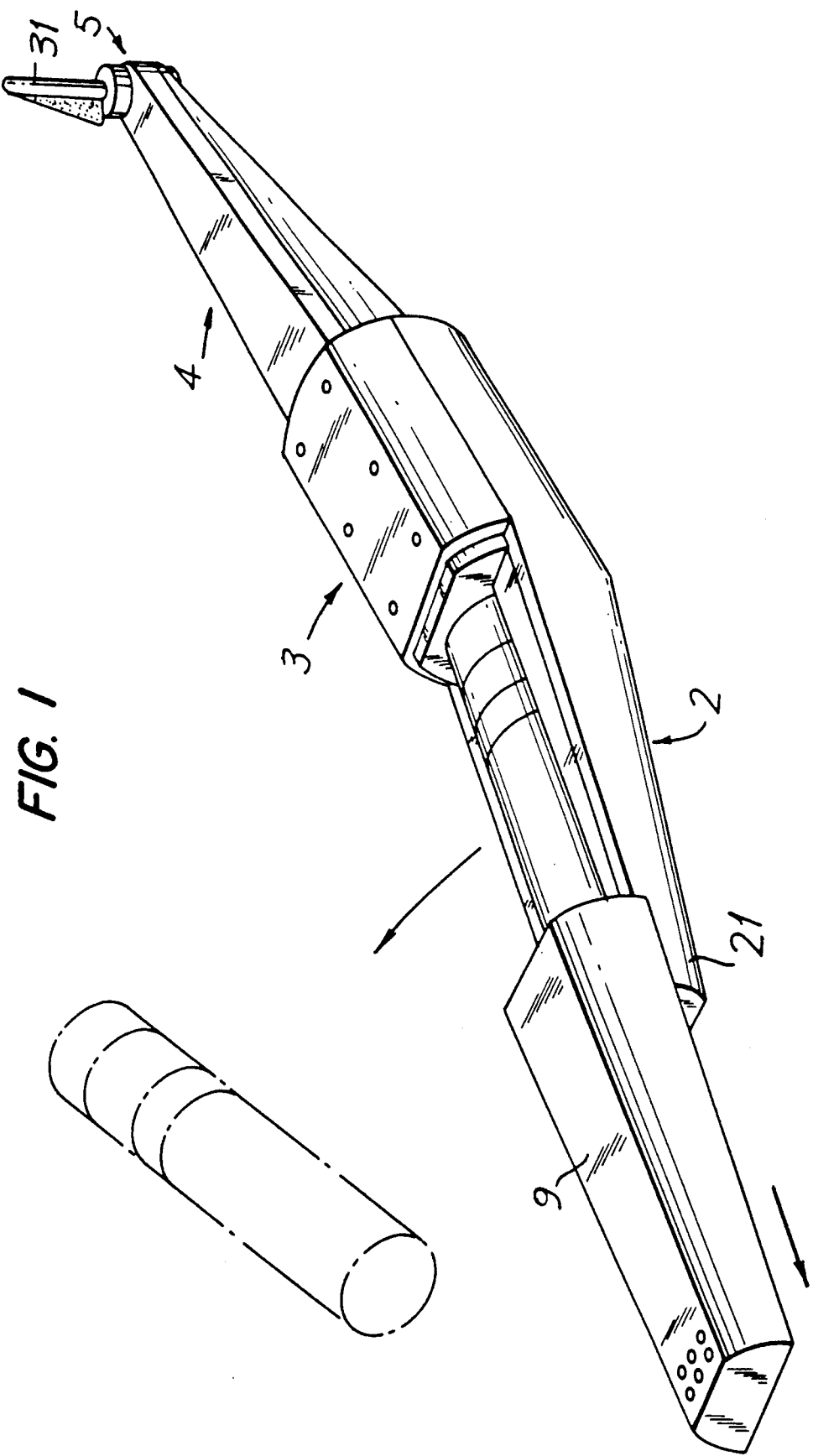
FIG. 1 is an isometric view of a self-powered dental hygiene device of this invention.
Figure 6:
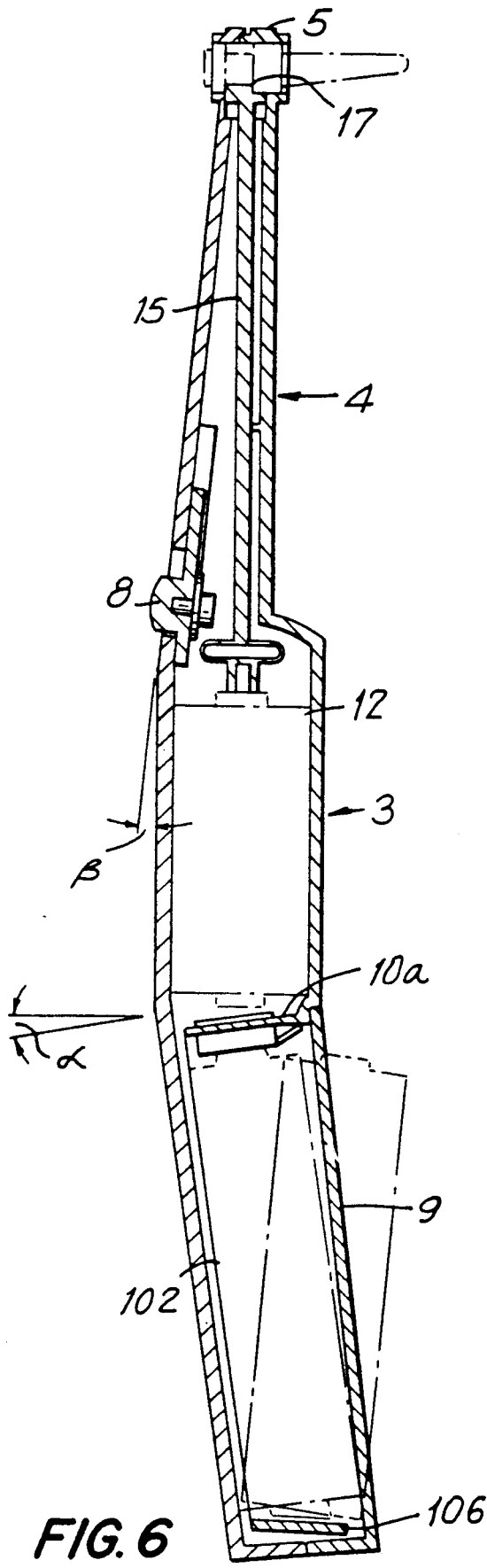
FIG. 6 is a cross-section view taken along lines A—A of FIG. 2.
Figure 4:
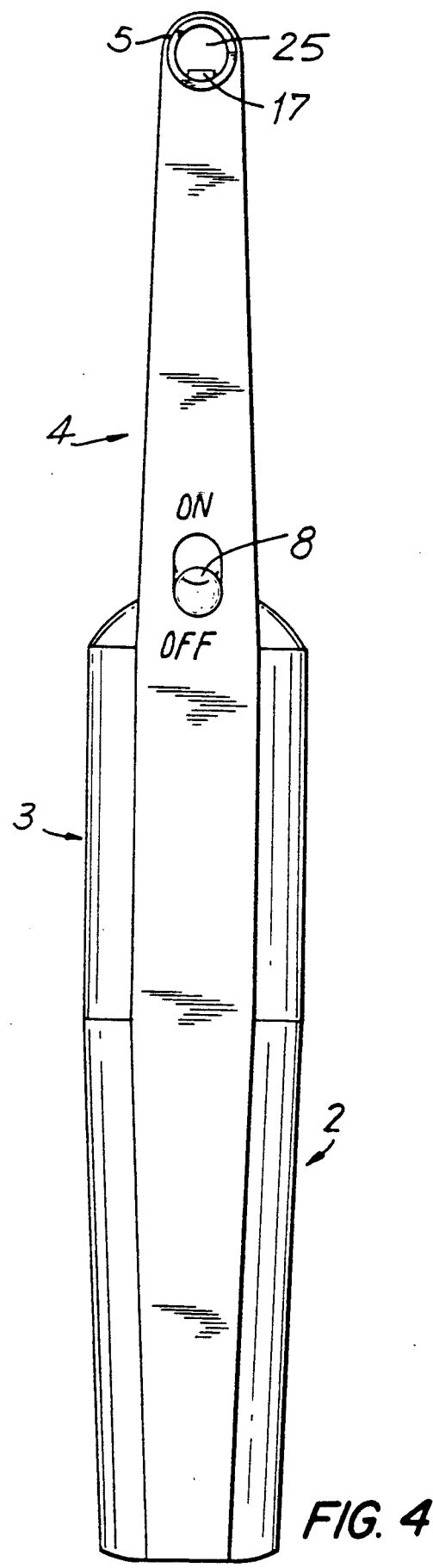
FIG. 4 is a top view of the tool of FIG. 1.
Figure 8:
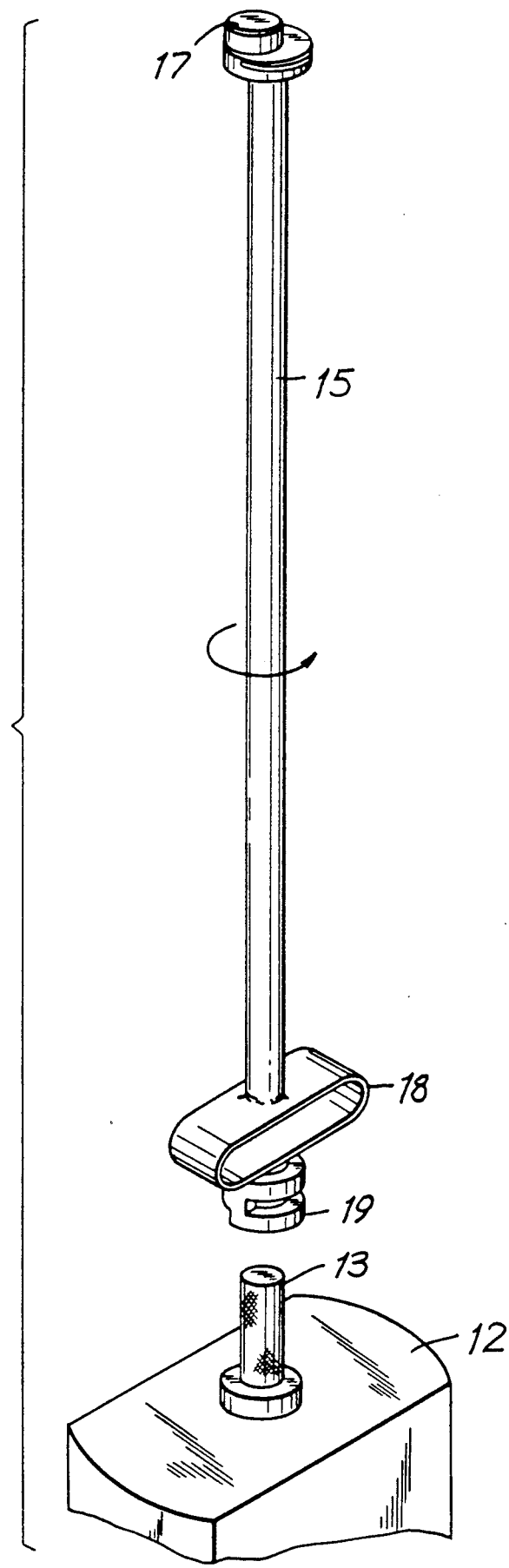
FIG. 8 is an enlarged exploded isometric view of the transmission system of the tool of FIG. 1.

The hand held device of the present invention is shown in preferred embodiments in the accompanying drawings Referring to the drawings, the outer housing, generally indicated by the numeral 1, is formed into a shape which is easily held and manipulated by a single adult human hand, and is thus suitable for single handed use. The housing comprises a wider, lower portion which forms the battery end section, generally indicated by the numeral 2, which is adjacent an electric motor central portion, generally indicated by the numeral 3, which is adjacent at its top end to a transmission section, generally indicated by the numeral 4, and a tool bit head 5, and which is formed as a preferably molded plastic unit.

The battery section end portion 2, includes a slidably removable cover 9, which can be removed to expose the interior of the battery section for replacement of commercially available, e.g., dry-cell, batteries. Alternatively, permanently affixed rechargeable batteries can be utilized with a recharging socket located at the bottom end 22. When the battery is permanently in place, the slidable cover section 9 need not be used and a permanently affixed portion provided.

Immediately adjacent the battery section 2 is the electric motor section 3, centrally located on the case, and in turn immediately adjacent the transmission section 4. The motor section 3 houses an electric motor 12, which is in electric circuit connection with a battery 102 in the battery section 2, and is mechanically linked to a transmission shaft 15 within the transmission section 4. The electric motor 12 is in switchable electric circuit connection to the battery terminals 10a, 10b, the circuit being closable by an on/off switch button slide 8, located in the case 1 at the boundary between the motor section 3 and transmission section 4.

In this preferred embodiment, the switch slide 8 includes a surface in contact with a spring loaded circuit connector 7a, located within the case 1, and thus when the button 8 slides towards the head 5 of the device, it presses inwardly on the spring loaded circuit connector 7a, in circuit switch 7b, to close the circuit and to permit electricity to flow from the battery 102 to the electric motor 12. Sliding the switch button 8 towards the battery section 2, releases the spring loaded circuit connector 7a, causing an interruption in the circuit and shutting off the motor 12. Alternatively, the switch can be pressed inwardly and in that position the switch button 7a is held in the closed circuit position, and springs back to the open circuit position when pressure is released. For certain circumstances, it may be preferable to require this type of spring-loaded switch, such that the operation of the motor immediately halts upon the releasing of the switch 8.

A battery is in place within the battery section 2 and releasably held such that the positive terminal of the battery is in direct contact with the circuit terminal 10b and the negative end of the battery is in direct connect with the other circuit terminal 10a. Electrical conductors connect the two terminals 10a, 10b to the electric motor 12 and to the switch 7a, 7b.

A transmission shaft 15 is slidably and rotatably held within the transmission section 4 by interior guide members 41a,b. The outer end of the transmission shaft 15 is secured to a radially extending transverse end portion 16, which includes an eccentrically located cam button 17, at the outer circumference of the transverse member 16.

A knurled driving shaft 13 (or other non-slip connection) extends axially outwardly from the electric motor towards the tool head 5. The driving shaft 13 extends into a centrally formed, mating female portion 19 affixed to the lower end of the transmission shaft 15. The interior surface of the female portion 19 firmly holds the knurled end 13 of the driving shaft so as to limit relative rotational slip between the surfaces.

The transmission shaft 15 further comprises an axially resilient member, such as the compression loop spring 18, preferably located adjacent the female holding member 19. The compression loop spring 18 permits limited resilient axial movement of the transmission shaft 15 within the transmission section 4. Alternatively, a helical spring can be provided between the motor driving shaft 13 and the transmission shaft female portion 19.

The transverse head member 16 and the eccentric cam button 17 extend into the head portion 5 of the tool case. The head portion 5 defines a central opening 25, extending through the tool case 1, in an axial direction transverse to the axis of the drive shaft 15. The eccentric cam button 17 extends into the transverse opening 25.

Rotary motion of the transmission shaft 15 is converted to linear reciprocating motion along a transverse axis, by the action of the eccentric cam button 17 between two annular surfaces on a transmission collar slidably held within the tool head portion 5. The collar can comprise two outer flanges, supporting the annular surfaces, and an intermediate neck portion of a smaller diameter. The eccentric cam button 17 can rotate between the two flanges, preferably out of contact with the neck portion.

Figure 9:
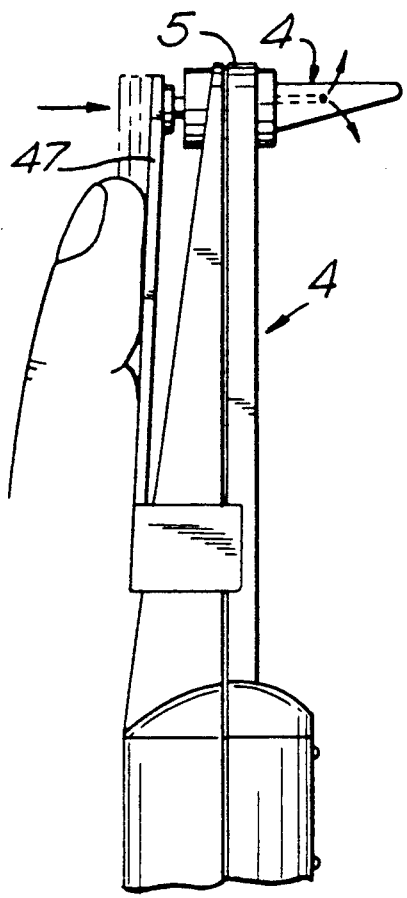
FIG. 9 is a partial side view of a tool with a fluid dispensing bit.
Figure 10A:
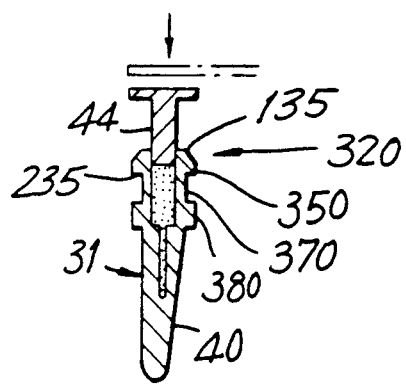
FIG. 10a is a cross-sectioned elevation view of the tool bit of FIGS. 9 and 10.
Figure 10:
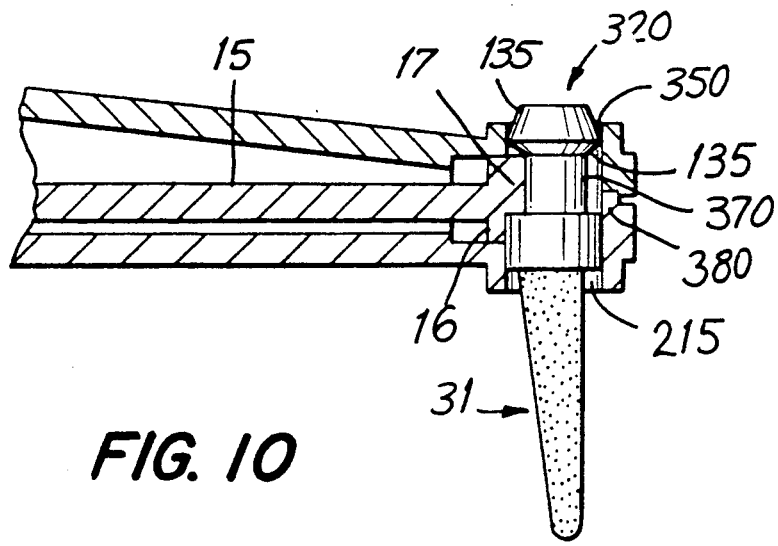
FIG. 10 is a cross-sectioned partial side elevation view of the head portion of the tool of this invention with a fluid dispensing embodiment of a dental tool bit in place.

Referring to the embodiment of FIGS. 9, 10 and 10a, a transmission collar, generally indicated by the numeral 320, is formed integral with the tool bit 31. The collar 320 comprises a beveled outer flange 350 and an inner flange 380 surrounding a collar shank 370. The eccentric cam button 17 extends between the two flanges 350, 380.

Dental tool bits, for example, the paste-dispensing bit 31 shown in the drawings, are designed to be of various shapes and surface textures for dislodging of films of food particles and micro-organisms from various teeth surfaces and are held within the central head aperture 25.

In the embodiment of FIGS. 9 and 10, when the bit is attached, into the head portion 5, the outer flange 350 is pushed first into the bottom opening of the central head aperture 25. The beveled outer end 135 of the outer flange 350 pushes against the eccentric cam button 17 causing the transmission shaft 15 to move axially towards the electric motor 12, compressing the spring loop 18 until the outer flange 350 moves beyond the button 17 and the button springs back and is supported adjacent the collar shank 370, between the two flanges 350, 380. When the tool bit 31 is removed, the inner bevel 235 pushes aside the cam button 17. The bit 31 is thus releasably retained within the aperture 25 by the eccentric cam button 17.

In the embodiment of FIG. 11, a permanent collar, generally indicated by the numeral 32 is secured in to the head portion aperture 25, so as to be reciprocally movable. The collar 32 comprises an outer flange 35 and an inner flange 38, with a shank 37 (of lesser diameter) therebetween. The eccentric cam button 17 extends towards the collar shank 37 between the two flanges 35, 38. A central opening 135 through the permanent collar 32 can receive a second embodiment of a tool bit generally indicated by the numeral 45. Extending from the inner flange 38 is a notched sleeve 40, the notches 140 opening outwardly, the sleeve defining the end of the central opening 135. The collar 32 can be restrained from rotating by a detent means interacting with a mating portion on the interior surface of the head aperture 25, e.g. a wedged sphere 156 in the interior surface and an axially extending notch 158 on the outer surfaces of the flanges 35, 38, or by forming the interior cross-section of the head aperture 25 and exterior cross-section of the collar 32 to be mating polygons, or to be other than circular. It is noted that in this embodiment there is no need for a compression spring in the transmission shaft 15, as the shaft 15 need not be axially movable. In a combination situation, a semi-fixed collar can be removably juxtaposed with a resiliently movable shaft 15 to enable alternative use of the two types of tool bits shown above, 45, 31.

The tool bit 45, in the embodiment of FIG. 11, can be formed, e.g., of a hard, but flexible, thin molded plastic, such as polycarbonate. The blade portion 49 has opposing major surfaces which can be triangular in plan, tapering to a rounded bottom apex 51. One edge of the blade 49 is preferably thinner, to ease insertion between teeth. The major surfaces can be textured, or coated with fine abrasive particles.

The shank 52 of this bit is substantially cylindrical from the top of the blade 49 to the end 53. A slightly enlarged, annular rib 54 is formed adjacent the top end to mate with the annular notch, 155, formed on the interior of the fixed collar 32. The blade shank 52 is split through its upper portion by a slit 56, so that the shank can be compressed while being inserted into the fixed collar 32, and will then snap back so that the rib 54 locks into the notch 154, to axially secure the bit 45 relative to the collar 32.

A resilient spur 55 is formed at the top of the blade 49, and mates with any of the a notches 140 to pre-set the angular relationship between the bit blade 49 and the hand piece transmission shaft axis, "X".

In the most preferred embodiments, the tool bit 31, 45 is capable of being pre-filled with a unit dosage amount of a fluid material, such as tooth paste, or the like cleansing fluid. In this embodiment, a plunger 44, for example, can be provided, which when pressed will force any fluid held within a plenum chamber 45, within the bit to be discharged through thin pores formed through the wall of the blade 40. The plunger 44 can be pressed directly by the operator's finger or by a resilient arm, secured to the outer housing of the transmission portion 4 (as shown in FIG. 9); such a resilient arm 47 can provide desirable helpful leverage especially for users with small hands, or short fingers. Such a plunger 44 can be provided with any embodiment of the tool bit, i.e., with an integral collar (bit 31) or for use with a fixed collar (bit 45).

The ability to either preset the relative angle between the blade and the handle enables the user to comfortably hold the handpiece regardless of the location in the mouth to be cleaned. When a slightly greater versatility is required and when the effort required to dislodge, e.g., a piece of hard food caught in the teeth, is not needed, the bit can be permitted to freely rotate by not engaging the rotation resisting members (e.g., the spur 55 and notches 140).

The tool housing 1, described herein and as shown in the drawings, is designed to be easily held in a single hand of the user; thus, the widest point of the battery portion 2 of the housing, which comprises the principal handle, should be sufficiently narrow to be easily held during use. The transmission section 4 is preferably angled with respect to the battery section 2, and extends a sufficient distance from the motor section 3 to permit applying a dental tool bit 31 supported from the head aperture 25 to reach even the rear molars of the user. Thus, the transmission section 4 is preferably from about 4 ins. to about 6 ins. in length to accommodate the longest dental arch. The transmission section 4 and the electric motor section 3 are substantially coaxial. Preferably, the angle $\alpha$) between the axis of the motor section 3 and transmission section 4 and the axis of the battery section 2 is preferably at least about 6°, and most preferably in the range of from about 7 to about 12 degrees, to provide the desired ease of reaching any teeth in the mouth. The angle between the top surface of the motor portion 3 and the transmission portion top surface 4 is in the range of from about 4 degrees to about 8 degrees. (Angle B)

The bottom end surface 21, is so juxtaposed with respect to the axis of the battery portion 2, as to permit standing the dental device on its end. The angle of the bottom end surface 21 relative to the axis of the battery section 2 is dependant upon the location of the center gravity of the overall device, when the battery and a tool bit are in place. The center of gravity must be directly above, preferably, a central portion of the base surface 21.

In operation, after a tool bit (31 or 45) has been pressed into position through the head aperture 25, and the cam button 17 is in place between the collar flanges (35, 38 or 350, 380), the switch 8 is slid towards the head 5, starting the electric motor. Rotation of the driving shaft 13 in turn causes rotation of the transmission shaft 15, causing the eccentric cam button 17 to rotate and to move axially with respect to the tool bit shank portion 37, pressing against the opposed flange surfaces. As the eccentric button 17 rotates and moves transversely to the transmission shaft 15, the tool bit 31 is caused to move reciprocatingly axially, thereby creating the desired reciprocating movement for the tool blade 49.

The tool bit blade 49 is preferably formed of a flexible material, such as a plastic, and preferably has a textured or abrasive outer surface. Blades for the final polishing of tooth surfaces can be formed of natural material, such as a laminate of soft leather, or synthetic such surface films. The dental tool bits useful with this invention can include any of the devices set forth for example in co-pending application Ser. No. 172,483 filed on Mar. 24, 1988 or application Ser. No. 179,332 filed on Apr. 8, 1988, the description of the bits being incorporated herein by reference. As in the copending applications referred to above, the bit can rotate about its own longitudinal axis relative to the tool head 5, or the bit can be releasably restrained from rotating by the various means described herein and in the above referred to copending applications.

It is further advantageous to provide for the application of therapeutic fluid while operating the tool bit. The tool bit is formed with at least one thin edge which can fit into the interdental spaces. Tool bits capable of providing for the simultaneous application of, e.g., cleansing material such as toothpaste through the walls of the blade from an internal plenum space are also described for example, in the two copending applications referred to above One example of such a dispensing bit is shown in FIG. 10a, herewith.

In a preferred embodiment the battery provided for the energizing of the electric motor is a conventional AA dry cell battery (1.5 volts output). It has been found that a power output not exceeding about 4 volts, e.g., the power output provided by two such AA batteries, is sufficient to power a tool bit for cleaning the teeth, but is not sufficient to cause injury to the teeth or gum tissue. A tool bit jammed between two teeth can halt the rotary motion of the electric motor before causing injury to the user, either to the gums or to the teeth. A rechargeable battery of about the same voltage can, of course, also be used.

The dental tool of this invention is useful for the cleaning of any mammalian teeth, finding valuable use in veterinary medicine, as well.

It is also useful in a more powerful version, by increasing battery voltage or by connection to an external electrical source, for hobbyists use, as for smoothing wood or plastic, or even metal.

The patentable embodiments which are claimed are as follows:

1. A self-powered, hand-held dental device for the cleaning of teeth, the dental device comprising an outer housing; a portion of the outer housing providing a hand grip for the device; within the housing there being provided a battery section, a motor section, a transmission section and a tool bit head section; the battery section comprises a positive and a negative terminal, so juxtaposed as to retain a battery within the housing, disposed within the motor section of the housing; an electric motor provided with a driving member; switchable electric circuit means connecting the electric motor with the terminals and a switching means exposed to the exterior of the housing and so juxtaposed with the electrical circuit means as to cause the opening and closing of a circuit gap upon operation of the switch so as to initiate and terminate operation of the electric motor when an electric battery is provided between the terminals; the head section defining a transverse aperture therethrough, and located at the end of the transmission section distal the electric motor section; a rotatable transmission shaft held rotatably in the transmission section, one end of which is in mechanical operating connection with the electric motor driving member, the distal end of the transmission shaft comprising an eccentric cam member located radially outwardly of the axis of rotation of the transmission shaft and extending longitudinally out of the transmission shaft, but parallel to the axis of the transmission shaft, the eccentric cam member extending into the head section aperture, the aperture extending along an axis transverse to the axes of the transmission shaft and the cam; and a tool bit, comprising a tool head and a tool blade, and an internal surface defining a hollow plenum designed to hold a fluid and extending from within the tool head to at least a portion of the tool blade, and pores through the wall of the blade portion to permit passage of fluid held within the plenum out to the outside surface of the blade, and means secured to the dental tool designed to cause the expression through the pores of any fluid in the plenum; the tool bit being in operating relationship to the eccentric cam member, such that rotation of the transmission shaft causes reciprocating movement of the tool bit transversely to the transmission shaft axis.

2. The dental device of claim 1, wherein the tool head comprises a narrow shank neck and a larger diameter flange at each end of the shank neck, the shank neck being held within the head aperture and in proximal relationship to the eccentric cam.

3. The dental tool of claim 1, comprising a collar slidably secured to the tool head, the collar comprising a narrow central shank neck and an annular flange at each end of the shank neck, the eccentric cam member facing the shank neck between the two flanges, the collar defining a central aperture capable of holding the head of a tool bit in the operating relationship of the tool.

4. The dental device of claim 1 comprising a conduit means extending from the head end of the bit into the bit plenum to provide means for filling the bit plenum with fluid material and to provide means for applying compressive pressure to force the fluid out through the pores.

5. The dental device of claim 1 wherein the transmission section and shaft extend at an angle of from about 7° to about 12° with respect to the axis of the handle portion and wherein the head aperture extends substantially perpendicularly to the axis of the transmission shaft.

6. The dental device of claim 1 further comprising restraining means secured to the dental device for preventing relative rotation of the tool bit.

7. A self-powered hand-held dental device for the cleaning of teeth, the dental device comprising an outer housing; a portion of the outer housing providing a hand grip for the device; within the housing there being provided a battery section, a motor section, a transmission section and a tool bit head section; the battery section comprises a positive and a negative terminal so juxtaposed as to retain a battery within the housing; disposed within the motor section of the housing, an electric motor provided with a driving member; switchable electric circuit means connecting the electric motor with the terminals and a switching means exposed to the exterior of the housing and so juxtaposed with the electrical circuit means as to cause the opening and closing of a circuit gap upon operation of the switch so as to initiate and terminate operation of the electric motor when an electric battery is provided between the terminals; the head section defining a transverse aperture therethrough and located at the end of the transmission section, distal the electric motor section; a rotatable transmission shaft held rotatably within the transmission section, one end of which is in mechanical operating connection with the electric motor driving member, the distal end of the transmission shaft comprising an eccentric cam member located radially outwardly of the axis of rotation of the transmission shaft and extending longitudinally out of the transmission shaft but parallel to the axis of the transmission shaft, the eccentric cam member extending into the head section aperture, the aperture extending through the head section along an axis transverse to the axes of the transmission shaft and the cam; a tool bit, comprising a tool head and a tool blade, in operating relationship to the eccentric cam member, such that rotation of the transmission shaft causes reciprocating movement of the tool bit transversely of the shaft axis; and cooperating means on each of the tool bit and the head section designed to cooperatively releasably restrain the tool bit from rotating relative to the head section.

8. The dental tool of claim 7 wherein the dental bit comprises a hollow plenum within a blade portion and pores through the wall of the blade portion to permit passage of fluid held within the plenum out to the outside surface of the blade.

9. The dental tool of claim 7 wherein the cooperating means comprise a resilient spur and one or more mating notches.

10. The dental device of claim 7 further comprising a collar slidably secured within, and cocentric with, the head aperture, in operating relationship to the eccentric cam member, the collar comprising a narrow central shank neck and an annular flange at each end of the shank neck, the eccentric cam member facing the shank neck between the two flanges, the collar further comprising an internal surface defining a central aperture coaxial with the head aperture and designed to hold the head of the tool bit such that the tool bit moves axially with the collar relative to the dental tool, and wherein one of the cooperating means is rigidly secured to the collar.

11. The dental device of claim 10, comprising spring compression means between the eccentric cam and the motor driving member, to permit resilient axial movement of the transmission shaft when pressure is exerted against the cam having a component in a direction substantially parallel to the transmission shaft axis.

12. The dental device of claim 7, being powered by two AA dry cell batteries.

13. A self-powered, hand-held dental device for the cleaning of teeth, the dental device comprising a substantially integral outer housing; a portion of the outer housing providing a hand grip for the device; the housing defining, in serial axial juxtaposition, a battery section, a motor section, a transmission section, and a tool bit head section; the battery section containing a positive and a negative terminal so juxtaposed within the housing as to retain a battery within the housing; disposed within the motor section of the housing, an electric motor provided with a rotatable driving member; switchable electric circuit means connecting the electric motor with the terminals and a switching means exposed to the exterior of the housing and so juxtaposed with the electrical circuit means as to cause the opening and closing of a circuit gap upon operation of the switch so as to initiate and terminate operation of the electric motor when an electric battery is provided between the terminals; the head section defining a transverse aperture therethrough, and located at the end of the transmission section distal the electric motor section; a rotatable transmission shaft held rotatably in the transmission section, one end of which is in mechanical operating connection with the electric motor driving member, the shaft being coaxial with the driving member, the distal end of the transmission shaft comprising an eccentric cam surface located radially outwardly of the axis of rotation of the transmission shaft and extending longitudinally out of the transmission shaft but parallel to the axis of the transmission shaft, the eccentric cam member extending into the head section along an axis perpendicular to the axis of the transmission shaft; and a collar slidably secured within the head aperture, in operating relationship to the eccentric cam member, the collar defining a central aperture capable of holding the head of a tool bit such that the tool bit moves axially with the collar, the transmission section and shaft extend at an angle of from about 7 degrees to about 12 degrees with respect to the axis of the battery portion, and wherein the head aperture extends substantially perpendicularly to the axis of the transmission shaft.

14. The dental device of claim 13 wherein the transmission section and shaft extend at an angle of from about 7° to about 12° with respect to the axis of the handle portion and wherein the head aperture extends substantially perpendicularly to the axis of the transmission shaft.

15. The dental device of claim 14, comprising spring compression means between the eccentric cam and the motor driving member, to permit resilient axial movement of the transmission shaft when pressure is exerted against the cam having a component in a direction substantially parallel to the transmission shaft axis.

16. The dental device of claim 15, wherein the angle between the central plane of the top surface of the motor section and the central plane of the top surface of the transmission section is in the range of from about 4° to about 10°.

* * * * *